United States Patent [19]

Knight

[11] Patent Number: 4,927,641

[45] Date of Patent: May 22, 1990

[54] VETERINARY LINIMENT AND METHOD

[76] Inventor: Gerald L. Knight, 13106 McBurnett, Corpus Christi, Tex. 78410

[21] Appl. No.: 355,352

[22] Filed: May 23, 1989

[51] Int. Cl.$^5$ .............................................. A61K 33/14
[52] U.S. Cl. ..................................... 424/665; 514/936
[58] Field of Search ................. 424/661, 665; 514/936

[56] References Cited

U.S. PATENT DOCUMENTS 3,711,606  1/1973  Herschler .................. 514/936 X
4,035,483  7/1977  Bunyan ......................... 514/665
4,353,896  10/1982  Levy ............................ 514/936 X

*Primary Examiner*—Leonard Schenkman
*Attorney, Agent, or Firm*—G. Turner Moller

[57] ABSTRACT

A liniment for treating bowed tendons in horses comprises dimethylsulfoxide (DMSO) and an alkali metal hypochlorite, preferably sodium hypochlorite. The liniment is preferably a thin liquid but may be in the form of a lotion, gel or cream. The liniment is applied to the skin surrounding a damaged equine tendon.

9 Claims, No Drawings

VETERINARY LINIMENT AND METHOD

BACKGROUND OF THE INVENTION

This invention relates to a liniment and method of treating horses for bowed tendons.

Like any other animal, horses suffer soft tissue injuries. One type soft tissue injury is called a bowed tendon in which one of the major leg tendons is injured. Three common responses to tendon injuries are strain, contracture of the tendon and adhesion of the tendon to its sheath. A rare response to a tendon injury is rupture of the tendon. A bowed tendon heals by proliferation of the tissue around it, much like a bony callus forms. When the tendon does heal, it often adheres to things nearby. This abnormal adhesion of the tendon to adjacent tissues is the reason why the bowed tendon is a major problem which lasts so long.

The three major tendons in a horse's leg are the interosseus medius tendon or the suspensory ligament, the deep flexor tendon and the superficial flexor tendon. These tendons act as shock absorbers as the horse's hoof strikes the ground. These tendons normally are elastic enough to be effective, but abnormal stress causes collagen fibers and blood vessels within the tendons to tear. Most bowed tendons in race horses involve damage to the superficial flexor tendon.

In a bowed tendon, blood from ruptured vessels causes swelling along the back of the injured leg, thus the term "bowed." Symptoms range from minor soreness to lameness. Swelling is apparent in moderate to severe cases. Although horses are normally very fast healing animals, a bowed tendon does not normally heal easily because there is insufficient blood circulation into the damaged tendon. As the tendon heals, scar tissue forms adhering the tendon to the tendon sheath.

The standard treatment for a bowed tendon has been to fire the injured leg after the swelling has gone down, blistering the leg several times over the firing and then give the horse rest for at least one year. A great deal of time, effort and money is always tied up in a well trained race horse. Thus, the prospect of watching one's investment be idle for a year is unsatisfactory. Even worse, the future of world class athletes who have sat out for a year is dismal because very few ever again return to their prior performance level.

A more complete discussion of bowed tendons is found in an article entitled "Treating Tendon Trouble", The Blood-Horse of June 25, 1988, pp 3570-71. Disclosures of interest are in U.S. Pat. No. 4,353,896 and a book entitled DMSO, The True Story of a Remarkable Pain-Killing Drug by Barry Thrasis.

Dimethylsulfoxide (DMSO) is a highly polar, stable, hygroscopic organic liquid with exceptional solvent properties. DMSO easily penetrates the dermal barrier of animals and has been tested for use in certain types of topical preparations, e.g. see "Topical Pharmacology and Toxicology of Dimethyl Sulfoxide—Part I," Journal of the American Medical Association, Volume 193, No. 10, p 796 and literature cited therein. DMSO is a well known carrier for various topically applied medications and has the peculiar property of imparting a garlic or oyster taste in the mouth of the recipient within seconds of topical application.

In the course of this invention, applicant has tried DMSO alone on bowed tendons in horses. DMSO alone tends to reduce inflammation in the tendon, reduce swelling and give general relief to the horse but does not set the tendon, i.e. cause the tendon to harden and return to its pre-damaged condition. A horse treated with DMSO alone shows general improvement in a short period of time but reinjures the tendon almost immediately when put back to training or racing.

SUMMARY OF THE INVENTION

This invention comprises a liniment and treatment for bowed tendons in equines, especially thoroughbred horses, trotters or quarter horses which are raced. The liniment comprises DMSO, an alkali metal hypochlorite such as sodium hypochlorite, potassium hypochlorite and mixtures thereof and a diluent. The DMSO not only acts as a medium or penetrating solvent for transporting the alkali metal hypochlorite through the skin and other tissue to the injury site but also acts to reduce inflammation, improve blood circulation and reduce collagen accumulation. The DMSO is present in the range of 10-90% by volume, the alkali metal hydroxide is present in the range of 1-10% by volume and the balance comprises the diluent. The diluent is preferably water but may be other common topical applications, such as the lower alcohols, i.e. alcohols having from 1-4 carbon atoms, inclusive, of which isopropyl alcohol is the most commonly used.

In use, the DMSO performs its own healing function and serves to transport the alkali metal hypochlorite to the subcutaneous injury site in the damaged tendon. The liniment is applied to the skin around the injured tendon every day for a few days, preferably four. After initial application, the liniment is mixed with a material such as Ice-O-Gel, the mixture is applied generously to the injury and wrapped with cotton sheet and standing bandage. This is done every day for a few days, preferably four. After the secondary treatment, the trainer gyps or ponies the horse lightly to break adhesions between the tendon and tendon sheath. The treatment is repeated. At the end of sixteen days, the horse has likely recovered sufficiently to resume training.

The liniment of this invention can be in various forms such as lotions, creams, jellies, thin liquids, gels or aerosols. Depending on the desired form, the liniment may include one or more suspending agents such as sodium lauryl sulfate, stearyl alcohol, cetyl alcohol, glycerol monostearate, the polyethylene glycols and mixtures thereof. In the case of a lotion product, one or more emulsifiers may be employed.

It is accordingly an object of this invention to provide an improved treatment and liniment for bowed tendons in equines.

Another object of this invention is to provide a treatment and liniment for bowed tendons in equines incorporating DMSO and an effective amount of alkali metal hypochlorite.

These and other objects of this invention will become more fully apparent as this description proceeds, reference being made to the depending claims.

DESCRIPTION OF THE PREFERRED EMBODIMENTS

The liniments of this invention include an alkali metal hypochlorite, such as sodium hypochlorite, potassium hypochlorite and mixtures thereof. Preferably, the alkali metal hypochlorite is sodium hypochlorite. This component is preferably present at a level of up to about 10% by volume in the final liniment, more preferably from about 1-5% by volume and most preferably about 2.5% by volume.

The DMSO is advantageously used at a level of from about 5-90% by volume, more preferably from about 5-50% by volume and most preferably about 30% by volume.

Table I sets forth preferred components useful in the preparation of a thin liquid liniment in accordance with this invention. The ranges of use of the respective components are set forth, along with the most preferred amounts:

TABLE I

| Component | Usual Ranges (Vol. %) | Most Preferred (Vol. %) |
|---|---|---|
| DMSO | 5-90 | 30 |
| sodium hypochlorite | 1-10 | 2.5 |
| water | 0-90 | balance |
| isopropyl alcohol | 0-50 | — |

In preparing the liniment of this invention, a commercially available household bleach is obtained having a 5.25% solution of sodium hypochlorite in water. The bleach is mixed with distilled water to produce a mixture of diluted bleach of two parts bleach and one part distilled water. DMSO is slowly added to the diluted bleach to obtain the volumetric ratio of four parts DMSO to nine parts diluted bleach. Mixing of diluted bleach and DMSO is exothermic. Thus, DMSO is added to the diluted bleach rather than vice versa. The resultant liniment accordingly has the volumetric ratio of three parts distilled water, four parts DMSO and six parts household bleach.

A thin liquid type liniment as described is applied to a race horse having a bowed tendon as follows:

1. Apply two to three handfuls to the afflicted area around the damaged tendon once a day for four days. The tendon does not have to be cooled or wrapped. The front hooves should be shod with level end grips with the hoof at a 55° angle, the toe no longer than three inches from the coronet band. The rear hooves to be shod at a 50° angle.

2. After four days, mix three ounces of the preferred liniment with one half gallon of Ice-O-Gel, which is commercially available from Hawthorne Products, Dunkirk, Ind., shaking well. Apply generously by hand to the afflicted area moving the hand in the direction of hair growth, i.e. down. Do not rub in. Wrap with cotton sheet and standing bandage overnight. Repeat once a day for four days.

3. Gyp or pony lightly to break the adhesions. Repeat step 1 and then repeat step 2, totalling sixteen daily treatments in all. The animal should be substantially healed. Return the animal to training at the judgment of the trainer or veterinarian. If the animal is not healed, repeat steps 1 and 2 for an additional eight days treatment. To gyp a horse, one attaches a 35-40' rope to the horse's halter and walks or trots the horse in a circular motion about the trainer. To pony a horse, one man rides a second horse, leading the horse being treated. The treated horse is exercised around the track or exercise area thereby acting to break the adhesions between the tendon and sheath without the weight of the rider.

4. After morning training, apply Ice-O-Gel—liniment mixture as is step 2 for four days. For two days, apply alcohol to clean the leg and remove dried or excess liniment. On the seventh day, allow the legs to air dry. Repeat step 4 during training until race time until the trainer is confident the horse shows no effects of the damaged tendon.

By the second day of applying the liniment of this invention, there is normally a hardening of the damaged tendon. The tendon seems to draw down and there is a noticeable lessening of the swelling. The afflicted area begins to cool off, heat being a symptom of injury or strain. The horse becomes sounder in his movements.

With each succeeding application, the tendon becomes harder and sets. If there is a hole or tear in the tendon, new tissue appears to fill in and begin to knit the area together. By the fourth application, marked improvement will be seen both in the hardening of the tendon and the soundness of the horse. At this time all swelling and heat should be gone. A minimal amount of heat and swelling will return to the afflicted area when the adhesions are broken. This is normal and should occur only once. With each following application, the damaged tendon tightens and becomes sounder.

I claim:

1. A penetrating veterinary liniment comprising from about 1 to 10% by volume of an alkali metal hypochlorite; and from about 5 to 90% by volume DMSO, balance diluent.

2. The liniment of claim 1 wherein the alkali metal hypochlorite comprises sodium hypochlorite, potassium hypochlorite and mixtures thereof.

3. The liniment of claim 1 wherein the alkali metal hypochlorite is sodium hypochlorite.

4. The liniment of claim 1 wherein the diluent is water.

5. The liniment of claim 1 wherein the diluent comprises water and a lower alcohol having 1-4 carbon atoms.

6. The liniment of claim 1 wherein the DMSO is in the range of 5-50% by volume.

7. The liniment of claim 1 wherein the DMSO is on the order of about 30% by volume.

8. A method of treating bowed tendons in equines comprising applying to skin of the equine adjacent the bowed tendon a solution comprising from about 1 to 10% by volume of an alkali metal hypochlorite and from about 5 to 90% by volume DMSO, balance diluent.

9. The method of claim 8 wherein the alkali metal hypochlorite is sodium hypochlorite.

* * * * *